United States Patent [19]

Jones et al.

[11] 4,272,532
[45] Jun. 9, 1981

[54] 5-(OPTIONALLY SUBSTITUTED PHENYL)-6H-1,3,4-THIADIAZINE-2-AMINES

[75] Inventors: Winton D. Jones, Cincinnati; Francis P. Miller, Loveland, both of Ohio

[73] Assignee: Richardson-Merrell Inc., Wilton, Conn.

[21] Appl. No.: 71,954

[22] Filed: Sep. 4, 1979

[51] Int. Cl.³ .................................... A61K 31/54
[52] U.S. Cl. ............................ 424/246; 544/8
[58] Field of Search .................... 544/8; 424/246

[56] References Cited

U.S. PATENT DOCUMENTS

| | | | |
|---|---|---|---|
| 2,871,237 | 1/1959 | Gregory | 260/243 |
| 3,428,631 | 2/1969 | Trepanier et al. | 260/243 |
| 3,862,183 | 1/1975 | Doyle | 544/8 |
| 4,158,732 | 6/1979 | Cleveland et al. | 544/8 |

FOREIGN PATENT DOCUMENTS 49-88889 8/1974 Japan.

OTHER PUBLICATIONS

Ishizaka, "Chemical Abstracts", vol. 82, entry 59824t (1975) for Japanese Pat. No. 74-5439.
Derwent Abstract 80095v/46 for Japanese Pat. No. 74-88889.
Robbins et al, *Proc. Natl. Acad. Sci. U.S.*, vol. 24, pp. 141–145, (1938).
Ban, *J. Pharm. Soc. Japan*, vol. 73, pp. 533–537 (1953).
Bilinski et al, Chemical Abstracts, vol. 63, 18063 (1965).
Trepanier et al, *J. Med. Chem.*, vol. 10, No. 6, pp. 1085–1087, (1967).
Rao, *Khim. Geterotsikl. Soedin*, 1977 (3), pp. 291–310.
Klosa, *Arch. Pharm.*, vol. 287, pp. 12–14, (1954).

*Primary Examiner*—John M. Ford
*Attorney, Agent, or Firm*—John J. Kolano; Raymond A. McDonald; Salvatore R. Conte

[57] ABSTRACT

A method of inducing sedation in a patient comprises administering to a patient in which sedation is desired an amount effective for inducing sedation of a compound of the formula

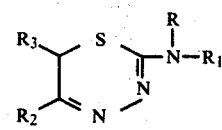

wherein
R is H, or $C_{1-5 \text{ or } 7}$-straight or branched chain alkyl;
$R_1$ is H, $C_{1-5 \text{ or } 7}$-straight or branched chain alkyl or allyl;
$R_2$ is phenyl or phenyl substituted with F, Cl, Br, $NO_2$, $C_{1-5}$ straight or branched chain alkyl, $C_{1-5}$ straight or branched chain alkoxy, 2,4-di-Cl, 2,4-di-F or 2,4-di-Br, with the proviso that when the phenyl group is monosubstituted with F, the F atom is not in the o-position; and
$R_3$ is H or C-1-5 straight or branched chain alkyl, with the proviso that when $R_3$ is straight or branched chain alkyl, $R_2$ is unsubstituted phenyl; or
a pharmaceutically acceptable acid addition salt thereof.

7 Claims, No Drawings

5-(OPTIONALLY SUBSTITUTED PHENYL)-6H-1,3,4-THIADIAZINE-2-AMINES

RELATIONSHIP TO OTHER APPLICATIONS

This application is related to copending application Ser. Nos. 071,952, 071,970, 072,793 and 071,966, all filed Sept. 4, 1979.

BACKGROUND OF THE INVENTION

The present invention relates to 5-(optionally substituted phenyl)-6H-1,3,4-thiadiazine-2-amines, having activity as sedatives.

As a general class, 5-(optionally substituted phenyl)-6H-1,3,4-thiadiazine-2-amines are known as chemical intermediates. See, for example, Japanese Pat. Nos. 74-110,696, 74-110,697 and 74-100,080. Many individual species within the scope of the compounds defined herein and also species related thereto are also known as chemical intermediates. See, for example:

1. Japanese Pat. No. 75 37651;
2. McLean et al, J. Chem. Soc. 1937, 556-9;
3. Avramovici, Analele stiint. univ. "Al. I. Cuza" Iasi, Sect. 1 (Mat. Fiz., chim.). (N.S.) 1, 315-319 (1955). CA51:10541;
4. Beyer et al, Justus Liebigs Ann. Chem. 741, 45-54 (1970);
5. Japanese Pat. No. 74-110,696;
6. Japanese Pat. No. 74-110,697;
7. Bose, Quart. J. Indian Chem. Soc. 1, 51-62 (1924).
8. Beyer et al, Chem. Ber. 89, 107-14 (1956);
9. Japanese Pat. No. 74-88,889;
10. Japanese Pat. No. 74-100,080;
11. Bose, Quart. J. Ind. Chem. Soc. 2, 95-114 (1925).
12. Bose et al, J. Indian Chem. Soc. 7, 733-9 (1930);
13. Bulka et al, Z. Chem. 15(12), 482 (1965);
14. Schmidt et al, Tetrahedron Lett. 1975 (1), 33-6;
15. Beyer, Quart. Rep. Sulfur Chem. 5(3), 177-89 (1970);
16. Saraswathi et al, Indian J. Chem. 10(12), 1151-4 (1972);
17. Hampel, Z. Chem. 9(2), 61-2 (1969);
18. Pfeiffer et al, Z. Chem. 17(6), 218-20 (1977);
19. Pfeiffer et al, Synthesis 1977(7), 485-6; and
20. Pfeiffer et al, Synthesis 1977(3), 196-8.

Certain species are further known as flame retardants (Japanese Pat. No. 74-5439).

Moreover, some 2-amino-1,3,4-thiadiazines are generally known to have antiviral, antiinflammatory and analgesic activity (Japanese Pat. No. 74-88889). Additionally, many individual species within the scope of those defined herein, as well as others related in structure are disclosed in this same reference. Some species have been found ineffective as vitamin B substitutes (Robbins et al, Proc. Natl. Acad. Sci. U.S. 24, 141-5 (1938) and antitubercular agents (Ban., J. Pharm. Soc. Japan 73, 533-7 (1953) and Bilinski et al, Bull. Acad. Polon. Sci., Ser. Sci. Chim. 13(6), 393-6 (1965)).

Other compounds having significantly different structures are also known to possess pharmacological activity.

4-methyl-4H-5,6-dihydro-1,3,4-thiadiazin-2-amines are known to be CNS active (U.S. Pat. No. 3,428,631 and Trepanier et al, J. Med. Chem. 10(6), 1085-7 (1967)). Additionally, 3-substituted-1,2-dihydro-1,3,4-thiadiazin-2-imines are known as slow cure accelerators for rubber (U.S. Pat. No. 2,871,237).

The 5-membered ring-containing 2-amino-1,3,4-thiadiazoles are known to possess CNS depressant activity (Maffii et al, Il Farmaco (Pavia) Ed. Sci. 13, 187-217 (1958); Great Britain Pat. No. 815,188; W. German Pat. No. 2,212,245 (or Great Britain Pat. No. 1,380,136); U.S. Pat. No. 3,965,110; U.S. Pat. No. 4,054,665; U.S. Pat. No. 3,919,428; and U.S. Pat. No. 3,992,396) and antihypertensive activity (U.S. Pat. No. 3,746,716).

These 5-membered ring-containing 1,3,4-thiadiazole-2-amines are a class of compounds treated by the prior art as distinct from the 6-membered ring-containing 1,3,4-thiadiazin-2-amines. However, the preparation of both types of compounds are reported together by Rao, Khim. Geterotsikl. Soedin. 1977(3), 291-310, as does Klosa, Arch. Pharm. 287, 12-14 (1954). In the latter reference, the compounds are reported as potential, but untested, tuberculostatics. Compounds of both types are also disclosed in Japanese Pat. No. 74 5439 as fire retardants.

SUMMARY OF THE INVENTION

A method of inducing sedation in a patient comprises administering to a patient in which sedation is desired an amount effective for inducing sedation of a compound of the formula

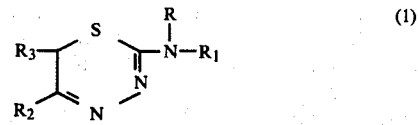

wherein
- R is H, or $C_{1-5 \text{ or } 7}$-straight or branched chain alkyl;
- $R_1$ is H, $C_{1-5 \text{ or } 7}$-straight or branched chain alkyl or allyl;
- $R_2$ is phenyl or phenyl substituted with F, Cl, Br, $NO_2$, $C_{1-5}$ straight or branched chain alkyl, $C_{1-5}$ straight or branched chain alkoxy, 2,4-di-Cl, 2,4-di-F or 2,4-di-Br, with the proviso that when the phenyl group is monosubstituted with F, the F atom is not in the o-position; and
- $R_3$ is H or $C_{1-5}$ straight or branched chain alkyl, with the proviso that when $R_3$ is straight or branched chain alkyl, $R_2$ is unsubstituted phenyl; or
- a pharmaceutically acceptable acid addition salt thereof.

DETAILED DESCRIPTION OF THE INVENTION

Illustrative examples of straight or branched chain $C_{1-5}$ alkyl groups mentioned above in all instances in describing the groups R, $R_1$, $R_2$ and $R_3$ include, for example, methyl, ethyl, n-propyl, isopropyl, n-butyl, sec-butyl, isobutyl, tert-butyl, n-pentyl, isopentyl, neopentyl, etc. Illustrative examples of straight or branched chain $C_7$ alkyl groups which R and $R_1$ may represent as used herein include, for example, n-heptyl, isoheptyl, etc.

Illustrative examples of straight or branched chain $C_{1-5}$ alkoxy groups mentioned as substituents for the $R_2$ phenyl group as used herein include, for example, methoxy, ethoxy, n-propoxy, isopropoxy, n-butoxy, isobutoxy, sec-butoxy, tert-butoxy, n-pentoxy, iso-pentoxy, neo-pentoxy, etc.

Pharmaceutically acceptable acid addition salts of the compounds of Formula I include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic and 2-phenoxybenzoic, or sulfonic acids such as, for example, methanesulfonic and 2-hydroxyethane-sulfonic acid.

Of the compounds of Formula I, those wherein $R_2$ is 2,4-dichlorophenyl, especially those wherein also $R_1$ is $C_{1-5}$ straight or branched chain alkyl or allyl are preferred. Thus, preferred compounds include 5-(2,4-dichlorophenyl)-N,N-dimethyl-6$\underline{H}$-1,3,4-thiadiazin-2-amine, 5-(2,4-dichlorophenyl)-N-(1-propyl)-6$\underline{H}$-1,3,4-thiadiazin-2-amine, 5-(2,4-dichlorophenyl)-N-2-propenyl-6$\underline{H}$-1,3,4-thiadiazin-2-amine and their acid addition salts.

Illustrative examples of compounds of this invention include, for example, N-methyl-5-phenyl-6$\underline{H}$-1,3,4-thiadiazin-2-amine, N-ethyl-5-phenyl-6$\underline{H}$-1,3,4-thiadiazin-2-amine, N-ethyl-5-(4-fluorophenyl)-6$\underline{H}$-1,3,4-thiadiazin-2-amine, N-ethyl-6-methyl-5-phenyl-6$\underline{H}$-1,3,4-thiadiazin-2-amine, 5-(4-fluorophenyl)-N-methyl-6$\underline{H}$-1,3,4-thiadiazin-2-amine, 6-methyl-5-phenyl-6$\underline{H}$-1,3,4-thiadiazin-2-amine, N,N,6-trimethyl-5-phenyl-6$\underline{H}$-1,3,4-thiadiazin-2-amine, 5-(2,4-dichlorophenyl)-N,N-dimethyl-6$\underline{H}$-1,3,4-thiadiazin-2-amine, 5-(2,4-dichlorophenyl)-N-(1-methylethyl)-6$\underline{H}$-1,3,4-thiadiazin-2-amine, 5-(2,4-dichlorophenyl)-N-(1-propyl)-6$\underline{H}$-1,3,4-thiadiazin-2-amine, 5-(4-chlorophenyl)-N-methyl-6$\underline{H}$-1,3,4-thiadiazin-2-amine, 5-(2-fluorophenyl)-N-methyl-6H-1,3,4-thiadiazin-2-amine, 5-(2,4-difluorophenyl)-N-methyl-6$\underline{H}$-1,3,4-thiadiazin-2-amine, 5-(2,4-dibromophenyl)-N-methyl-6$\underline{H}$-1,3,4-thiadiazin-2-amine and N-methyl-5-(2-nitrophenyl)-6$\underline{H}$-1,3,4-thiadiazin-2-amine, 5-(2,4-dichlorophenyl)-N-2-propenyl-6$\underline{H}$-1,3,4-thiadiazin-2-amine and the acid addition salts, e.g., the monohydrochloride, of each.

The compounds of this invention are useful as sedatives. These compounds can be administered to warm-blooded animals, mammals, rats, mice, dogs, cats, horses, pigs, cows, sheep, and humans. As used herein, the term "patient" is intended to mean the animal or mammal being treated.

The sedative-inducing activity of the compounds employed in the method of this invention may be illustrated by their effectiveness in standard pharmacological screening tests, e.g., by demonstrating an increase in the number of mice in a test group who take the side position upon administration.

The compounds employed in the process of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any sedation-inducing effective amount. The quantity of compound administered can vary over a wide range to provide from about 30 to about 50 mg/kg of body weight of the patient per day, to achieve the desired effect. Unit doses can contain about 5–500 mg of a compound of Formula I and may be administered, for example, from 1 to 4 times daily.

The compounds of Formula I are prepared by reacting a phenacyl halide of the formula

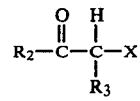

wherein X is Cl or Br, with a 4-substituted thiosemicarbazide of the formula

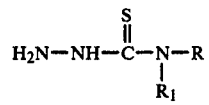

wherein R, $R_1$, $R_2$ and $R_3$ are as hereinbefore defined. The reaction is generally conducted in the presence of a solvent, e.g., a lower alkanol, such as, methanol, ethanol, isopropanol, n-propanol, n-butanol and the like, preferably methanol. The reaction time may vary from about 15 minutes to about 1 hour, preferably about 30 minutes, depending upon the reactants, the solvent and the reaction temperature which may vary from about 60° C. to about 80° C., preferably around 65° C. The product is generally worked-up by permitting the reaction mixture to cool and then concentrating it in vacuo. The resultant residue is recrystallized from an appropriate solvent, e.g., a mixture of a lower alkanol with, e.g., acetone, butanone of ethylacetate, e.g., methanol/acetone or methanol/ethylacetate, producing the compound of Formula I as its hydrohalide salt. Treatment with base produces a compound of Formula I.

Both the phenacyl halide and the 4-substituted thiosemicarbazide which are employed as starting materials in the preparation of the compounds of Formula I are either commercially available or, when unavailable, are very readily preparable by standard chemical reactions which are well-known to those of ordinary skill in the art. For example, the phenacyl halides may be prepared by halogenating the corresponding methyl (optionally-substituted)phenyl ketone using a sulfuryl halide, e.g., sulfuryl chloride, e.g., in acetic acid, e.g., to prepare the corresponding phenacyl chloride; or by reacting the corresponding optionally substituted benzene with a haloacetyl halide, e.g., chloroacetyl chloride via a Friedel Crafts reaction using an aluminum trichloride catalyst, e.g., to prepare the corresponding phenacyl chloride. The 4-substituted thiosemicarbazides may be prepared by conventionally reacting the appropriate substituted isothiocyanate with hydrazine in the presence, e.g., of diethyl ether.

EXAMPLES

The following examples are illustrative of the invention.

EXAMPLE 1

N-Methyl-5-phenyl-6$\underline{H}$-1,3,4-thiadiazin-2-amine hydrochloride 5.25 g (0.05 mole) of 4-methyl-thiosemicarbazide and 7.73 g (0.05 mole) of phenacyl chloride are heated and stirred at reflux (65° C.) in 200 ml of methanol for 30 minutes. At this time, the solvent is removed in vacuo. The residue is dissolved in methanol, warmed and then diluted with acetone. Subsequently, it is concentrated to a volume of approximately 200 ml. After standing for about 2 days, 8.33 g of N-methyl-5-phenyl-6H-1,3,4-thiadiazin-2-amine hydrochloride are deposited. m.p. 176°-178° C.

EXAMPLE 2

N-Ethyl-5-phenyl-6H-1,3,4-thiadiazin-2-amine hydrochloride 8.35 g (0.05 mole) of 4-ethyl-thiosemicarbazide and 9.95 g (0.05 mole) of phenacyl bromide are heated and stirred at reflux (65° C.) in 300 ml of methanol for 30 minutes. The solvent is removed in vacuo and the residue is recrystallized from methanol/acetone affording 8.2 g of N-ethyl-5-phenyl-6H-1,3,4-thiadiazin-2-amine hydrochloride. m.p. 169°-170.5° C. The product is then dried under high vacuum at 65° C.

EXAMPLE 3

N-Ethyl-5-(4-fluorophenyl)-6H-1,3,4-thiadiazin-2-amine hydrochloride 11.19 g (0.067 mole) of 4-ethyl-thiosemicarbazide and 17.6 g (0.1 mole) of (4-fluorophen)acyl chloride are heated and stirred at reflux (65° C.) in 400 ml of methanol for 30 minutes in a 1 liter round bottom flask equipped with a magnetic steering bar and a condenser protected by a CaCl$_2$ drying tube. The solution is allowed to cool to room temperature and is then concentrated. The residue is recrystallized from methanol/butanone, yielding 21.0 g (75.5%) of N-ethyl-5-(4-fluorophenyl)-6H-1,3,4-thiadiazin-2-amine hydrochloride. m.p. 192°-193° C. The solid is then dried under high vacuum at 65° C. overnight.

EXAMPLE 4

N-Ethyl-6-methyl-5-phenyl-6H-1,3,4-thiadiazin-2-amine hydrobromide 0.05 mole of α-methyl-phenacyl bromide and 0.05 mole of 4-ethyl-thiosemicarbazide are reacted using the procedure of EXAMPLE 1 to prepare 8.0 g of N-ethyl-6-methyl-5-phenyl-6H-1,3,4-thiadiazin-2-amine-hydrobromide. m.p. 174°-175° C. After recrystallization from methanol/ethyl acetate, the product is dried at 65° C. under high vacuum.

EXAMPLE 5

5-(4-Fluorophenyl)-N-methyl-6H-1,3,4-thiadiazin-2-amine hydrochloride 8.63 g of (4-fluorophen)acyl chloride and 4.66 g of 4-methylthiosemicarbazide are reacted using the conditions of EXAMPLE 1. The resultant product is recrystallized from methanol/ethyl acetate yielding 5.6 g of 5-(4-fluorophenyl)-N-methyl-6H-1,3,4-thiadiazin-2-amine hydrochloride. m.p. 139°-141° C. The product compound is dried under high vacuum at 65° C.

EXAMPLE 6

6-Methyl-5-phenyl-6H-1,3,4-thiadiazin-2-amine hydrobromide 0.05 mole of α-methyl-phenacyl bromide and 0.05 mole of thiosemicarbazide are heated and stirred at reflux (65° C.) in 200 ml of methanol for 30 minutes. The yellowish solution is concentrated in vacuo to produce a yellow solid. The solid is dissolved in methanol, diluted with ethyl acetate and then heated until crystallization ensues. The resultant solid is filtered yielding 6-methyl-5-phenyl-6H-1,3,4-thiadiazin-2-amine hydrobromide. m.p. 191°-192° C. The product is then dried at 65° C. under high vacuum.

EXAMPLE 7

N,N-6-Trimethyl-5-phenyl-6H-1,3,4-thiadiazin-2-amine hydrobromide 5.82 g (0.027 mole) of α-methyl-phenacyl bromide and 3.25 g (0.027 mole) of 4,4-dimethyl-thiosemicarbazide are heated and stirred at reflux (78.5° C.) in 200 ml of ethanol for 30 minutes. The solvent is removed in vacuo. The residual oil is dissolved in methanol/ethyl acetate and concentrated until a reddish colored gum precipitates. Refrigeration of the solution produces yellow crystals. This product is recrystallized from ethanol/butanone producing yellow crystals of N,N,6-trimethyl-5-phenyl-6H-1,3,4-thiadiazin-2-amine hydrobromide. m.p. 177°-179° C. The product is dried over methanol under high vacuum.

EXAMPLE 8

5-(2,4-Dichlorophenyl)-N,N-dimethyl-6H-1,3,4-thiadiazin-2-amine monohydrochloride 4.16 g (0.035 mole) of 4,4-dimethyl-thiosemicarbazide and 7.82 g (0.035 mole) of (2,4-dichlorophen)acyl chloride are reacted using the conditions of EXAMPLE 1. The resultant product is dissolved in ethyl acetate to produce fluffy yellow needles. These are recrystallized from methanol/ethylacetate and dried under high vacuum to produce 5-(2,4-dichlorophenyl)-N,N-dimethyl-6H-1,3,4-thiadiazin-2-amine monohydrochloride. m.p. 219°-222° C.

EXAMPLE 9

5-(2,4-Dichlorophenyl)-N-(1-methylethyl)-6H-1,3,4-thiadiazin-2-amine monohydrochloride 3.99 g (0.03 mole) of 4-isopropyl-thiosemicarbazide and 6.70 g (0.03 mole) of (2,4-dichlorophen)acyl chloride are reacted using the conditions of EXAMPLE 1 except only 150 ml of the methanol solvent are employed. The product is recrystallized from methanol/ethyl acetate twice, yielding 5-(2,4-dichlorophenyl)-N-(1-methylethyl)-6H-1,3,4-thiadiazin-2-amine monohydrochloride. m.p. 207°-208° C.

EXAMPLE 10

5-(4-Chlorophenyl)-N-methyl-6H-1,3,4-thiadiazin-2-amine monohydrobromide 5.83 g (0.025 mole) of (4-chlorophen)acyl bromide and 2.63 g of 4-methyl-thiosemicarbazide are reacted under the conditions of EXAMPLE 1 except that only 150 ml of the solvent methanol are employed. After concentration of the methanol solvent in vacuo, the residue is recrystallized from methanol/ethyl acetate. A second such recrystallization yields 5-(4-chlorophenyl-N-methyl-6H-1,3,4-thiadiazin-2-amine monohydrobromide. m.p. 179°-180° C.

EXAMPLE 11

5-(2-Fluorophenyl)-N-methyl-6H-1,3,4-thiadiazin-2-amine monohydrochloride 8.62 g of (2-fluorophen)acyl chloride and 5.22 g of 4-methylthiosemicarbazide are reacted in accordance with the conditions of EXAMPLE 1 except that only 150 ml of the methanol solvent are employed. After recrystallization from methanol/ethyl acetate, 6.7 g of 5-(2-fluorophenyl)-N-methyl-6H-1,3,4-thiadiazin-2-amine monohydrochloride are obtained. m.p. 183°–184° C.

EXAMPLE 12

5-(2,4-Difluorophenyl)-N-methyl-6H-1,3,4-thiadiazin-2-amine monohydrochloride 7.62 g (0.04 mole) of (2,4-difluorophen)acyl chloride and 4.20 g (0.04 mole) of 4-methyl-thiosemicarbazide are heated with stirring under reflux (78.5° C.) in 200 ml of ethanol. The solvent is concentrated in vacuo and the residue is recrystallized from methanol/ethyl acetate two times. It is then recrystallized from methanol/butanone, producing 5-(2,4-difluorophenyl)-N-methyl-6H-1,3,4-thiadiazin-2-amine monohydrochloride. m.p. 182°–184° C. The product is dried at 65° C. under high vacuum.

EXAMPLE 13

5-(2,4-Dibromophenyl)-N-methyl-6H-1,3,4-thiadiazin-2-amine monohydrochloride 2.1 g (0.0077 mole) of (2,4-dibromophen)acyl chloride and 0.81 g (0.0077 mole) of 4-methyl-thiosemicarbazide are heated and stirred at reflux in 150 ml of methanol for 35 minutes. After concentration of the solvent, a yellow foamy gum is produced. The gum is dissolved in methylene chloride/methanol/ethyl acetate. The solvent is concentrated, producing a gum which, upon scratching and cooling, slowly becomes a solid. The solid is filtered and dried at 78° C. under high vacuum, yielding 5-(2,4-dibromophenyl)-N-methyl-6H-1,3,4-thiadiazin-2-amine monohydrochloride. m.p. 184°–186° C.

EXAMPLE 14

N-Methyl-5-(2-nitrophenyl)-6H-1,3,4-thiadiazin-2-amine monohydrobromide 9.2 g (0.0375 mole) of (2-nitrophen)acyl bromide and 3.5 g (0.03 mole) of 4-methyl-thiosemicarbazide are heated and stirred at reflux in 250 ml of methanol. The solution is concentrated and a solid crystallizes out. The solid is recrystallized from methanol/ethanol and filtered. The resultant powder is recrystallized from methanol/ethyl acetate to produce 3.8 g of N-methyl-5-(2-nitrophenyl)-6H-1,3,4-thiadiazin-2-amine monohydrobromide. m.p. 229°–230° C.

EXAMPLE 15

5-(2,4-Dichlorophenyl)-N-2-propenyl-6H-1,3,4-thiadiazin-2-amine monohydrochloride 3.93 g (0.03 mole) of 4-allyl-thiosemicarbazide and 7.00 g (0.03 mole) of (2,4-dichlorophen)acyl chloride and reacted in accordance with the conditions of EXAMPLE 1. Recrystallization from methanol/methyl acetate produces 8 g of 5-(2,4-D-dichlorophenyl)-N-2-propenyl-6H-1,3,4-thiadiazin-2-amine m.p. 188°–189° C.

EXAMPLE 16

5-(2,4-dichlorophenyl)-N-(1-propyl)-6H-1,3,4-thiadiazin-2-amine monohydrochloride Analogously to EXAMPLE 1, 3.99 g (0.03 mole) of 4-n-propyl-thiosemicarbazide and 6.70 g (0.03 mole) of (2,4-dichlorophen)acyl chloride are reacted. After recrystallization from methanol/methyl acetate, 6.4 g of 5-(2,4-dichlorophenyl)-N-(1-propyl)-6H-1,3,4-thiadiazin-2-amine are obtained. m.p. 184°–185° C.

EXAMPLE 17

An illustrative composition for tablets is as follows:

|     |                                                                              | Per Tablet |
| --- | ---------------------------------------------------------------------------- | ---------- |
| (a) | 5-(2,4-Dichlorophenyl)-N,N-dimethyl-6H-1,3,4-thiadiazin-2-amine monohydrochloride | 100.0 mg |
| (b) | wheat starch                                                                 | 15.0 mg    |
| (c) | lactose                                                                      | 33.5 mg    |
| (d) | magnesium stearate                                                           | 1.5 mg     |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 18

An illustrative composition for a parenteral injection is the following wherein the quantities are on a weight to volume basis.

|     |                                                                              | Amount |
| --- | ---------------------------------------------------------------------------- | ------ |
| (a) | 5-(2,4-Dichlorophenyl)-N,N-dimethyl-6H-1,3,4-thiadiazin-2-amine monohydrochloride | 100.0 g |
| (b) | sodium chloride                                                              | q.s.   |
| (c) | water for injection to make                                                  | 20 ml  |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 19

An illustrative composition for hard gelatin capsules is as follows:

|     |                                                                              | Amount |
| --- | ---------------------------------------------------------------------------- | ------ |
| (a) | 5-(2,4-Dichlorophenyl)-N,N-dimethyl-6H-1,3,4-thiadiazin-2-amine monohydrochloride | 200.0 mg |
| (b) | talc                                                                         | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 20

An illustrative composition for pills is the following:

|     |                                                                              | Per Pill |
| --- | ---------------------------------------------------------------------------- | -------- |
| (a) | 5-(2,4-Dichloropheny)-N,N-dimethyl-6H-1,3,4-thiadiazin-2-amine monohydrochloride | 200 mg |
| (b) | corn starch                                                                  | 130 mg   |
| (c) | liquid glucose                                                               | 20 ml    |

The pills are prepared by blending the active ingredient (a) and the corn starch and then adding the liquid glucose with thorough kneading to form a plastic mass from which the pills are cut and formed.

Treatment of each of the compounds of EXAMPLES 1–16 with base, e.g., aqueous NaOH, produces the corresponding free amine of Formula 1 which after isolation and purification in the conventional manner, can be substituted for the hydrochloride salt employed in each of EXAMPLES 17–20.

EXAMPLE 21

The compounds of the preceding examples can be administered as a sedative for the treatment of, e.g., insomnia, preoperative, obstetrical and daytime sedation.

Sedation is inducible in mice under conditions comparable to that employed by administration of diazepam (Valium) parenterally (i.v.). For example, the compound of Example 1 or 3 has about 1/7 the potency of diazepam, whereas the compound of Example 8 has about ¼ the potency of diazepam, under similar conditions of parenteral administration. Therefore, the compound under consideration will be administered to humans for the same indications and under the same dosage conditions (adjusted for differential potency) as those seen in mice for diazepam. For example, the compound of Example 8 can be administered orally in doses of 1050 mg., 2 to 4 times daily, for beneficial sedative effect.

I claim:

1. A method of inducing sedation in a patient which comprises administering to a patient in which sedation is desired an amount effective for inducing sedation of a compound of the formula

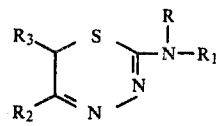

wherein
R is H, or $C_{1-5 \text{ or } 7}$-straight or branched chain alkyl;
$R_1$ is H, $C_{1-5 \text{ or } 7}$-straight or branched chain alkyl or allyl;
$R_2$ is phenyl or phenyl substituted with F, Cl, Br, $No_2$, $C_{1-5}$ straight or branched chain alkyl, $C_{1-5}$ straight or branched chain alkoxy, 2,4-di-Cl, 2,4-di-F, 2,4-di-Br with the proviso that when the phenyl group is monosubstituted with F, the F atom is not in the o-position; and
$R_3$ is H or $C_{1-5}$ straight or branched chain alkyl, with the proviso that when $R_3$ is straight or branched chain alkyl, $R_2$ is unsubstituted phenyl; or
a pharmaceutically acceptable acid addition salt thereof.

2. The method of claim 1, wherein the amount of the active compound which is administered is 30–50 mg/kg of patient body weight per day.

3. The method of claim 1, wherein the compound administered is one wherein $R_2$ is 2,4-dichlorophenyl.

4. The method of claim 3, wherein the compound administered is one wherein $R_1$ is $C_{1-5}$ straight or branched chain alkyl or allyl.

5. The method of claim 1, wherein the compound administered is 5-(2,4-dichlorophenyl)-N,N-dimethyl-6H-1,3,4-thiadiazin-2-amine monohydrochloride.

6. The method of claim 1, wherein the compound administered is 5-(2,4-dichlorophenyl)-N-(1-propyl)-6H-1,3,4-thiadiazin-2-amine monohydrochloride.

7. The method of claim 1, wherein the compound administered is 5-(2,4-dichlorophenyl)-N-2-propenyl-6H-1,3,4-thiadiazin-2-amine.

* * * * *